US008382780B2

(12) United States Patent
Birk

(10) Patent No.: US 8,382,780 B2
(45) Date of Patent: Feb. 26, 2013

(54) FATIGUE-RESISTANT GASTRIC BANDING DEVICE

(75) Inventor: Janel Birk, Oxnard (CA)

(73) Assignee: Allergan, Inc., Irvine, CA (US)

( * ) Notice: Subject to any disclaimer, the term of this patent is extended or adjusted under 35 U.S.C. 154(b) by 293 days.

(21) Appl. No.: 12/851,437

(22) Filed: Aug. 5, 2010

(65) Prior Publication Data

US 2010/0324359 A1 Dec. 23, 2010

Related U.S. Application Data

(63) Continuation of application No. 10/492,784, filed on Apr. 18, 2005, now Pat. No. 7,811,298.

(60) Provisional application No. 60/407,219, filed on Aug. 28, 2002.

(51) Int. Cl.
*A61B 17/08* (2006.01)
*A61F 2/02* (2006.01)
*A61F 2/00* (2006.01)

(52) U.S. Cl. .............................. 606/157; 600/31; 600/37

(58) Field of Classification Search .................. 606/151, 606/201–203, 157; 600/37, 31
See application file for complete search history.

(56) References Cited

U.S. PATENT DOCUMENTS

| 1,174,814 | A | 3/1916 | Brennan et al. |
| 1,830,947 | A | 11/1931 | Klingel |
| 1,999,683 | A | 4/1935 | Borresen |
| 2,163,048 | A | 6/1939 | McKee |
| 2,339,138 | A | 1/1944 | Black |
| 2,405,667 | A | 8/1946 | Ottesen |
| 2,438,231 | A | 3/1948 | Schultz et al. |
| 2,635,907 | A | 4/1953 | Heimbuch |
| 2,714,469 | A | 8/1955 | Carlson |
| 2,936,980 | A | 5/1960 | Rapata |
| 3,059,645 | A | 10/1962 | Hasbrouck et al. |
| 3,189,961 | A | 6/1965 | Heller |
| 3,667,081 | A | 6/1972 | Burger |
| 3,840,018 | A | 10/1974 | Heifetz |
| 3,955,834 | A | 5/1976 | Ahlrot |
| 4,053,176 | A | 10/1977 | Hilbush |
| 4,118,805 | A | 10/1978 | Reimels |
| 4,133,315 | A | 1/1979 | Berman et al. |
| 4,157,713 | A | 6/1979 | Clarey |

(Continued)

FOREIGN PATENT DOCUMENTS

| CA | 949965 | 6/1974 |
| CN | 1250382 | 4/2000 |

(Continued)

OTHER PUBLICATIONS

Brown et al; "Symmetrical Pouch Dilation After Laparoscopic Adjustable Gastric Banding: Incidence and Management"; Obesity Surgery; V. 18, pp. 1104-1108; 2008.

(Continued)

*Primary Examiner* — Julian Woo
(74) *Attorney, Agent, or Firm* — Linda Fox; Stephen Donovan; Debra Condino

(57) ABSTRACT

A fatigue-resistant inflatable gastric banding device suitable for laparoscopic placement around the stomach of a patient for the treatment of obesity and a method for such treatment are disclosed. The device includes a gastric band having a chambered inflatable member, substantially coextensive with an inner stomach facing surface of the band, that does not crease, wrinkle or fold when adjusted, so as to present a substantially smooth contour along the inner circumference, and to avoid fatigue or failure of the member itself. A gastric band having multiple inflatable compartments or chambers, which may be inflated together or individually is also disclosed.

12 Claims, 6 Drawing Sheets

U.S. PATENT DOCUMENTS

| | | | |
|---|---|---|---|
| 4,176,412 A | 12/1979 | Peterson | |
| 4,236,521 A | 12/1980 | Lauterjung | |
| 4,271,827 A | 6/1981 | Angelchik | |
| 4,299,012 A | 11/1981 | Oetiker | |
| 4,340,083 A | 7/1982 | Cummins | |
| 4,399,809 A | 8/1983 | Baro et al. | |
| 4,408,597 A | 10/1983 | Tenney, Jr. et al. | |
| 4,417,567 A | 11/1983 | Trick | |
| 4,424,208 A | 1/1984 | Wallace et al. | |
| 4,442,153 A | 4/1984 | Meltsch | |
| 4,450,375 A | 5/1984 | Siegal | |
| 4,485,805 A | 12/1984 | Foster, Jr. | |
| 4,492,004 A | 1/1985 | Oetiker | |
| 4,551,862 A | 11/1985 | Haber | |
| 4,558,699 A | 12/1985 | Bashour | |
| 4,559,699 A | 12/1985 | Owen et al. | |
| 4,582,640 A | 4/1986 | Smestad et al. | |
| 4,582,865 A | 4/1986 | Balazs et al. | |
| 4,592,339 A | 6/1986 | Kuzmak et al. | |
| 4,592,355 A | 6/1986 | Antebi | |
| 4,601,713 A | 7/1986 | Fuqua | |
| 4,667,672 A * | 5/1987 | Romanowski | 606/202 |
| 4,671,351 A | 6/1987 | Rappe | |
| 4,693,695 A | 9/1987 | Cheng | |
| 4,694,827 A | 9/1987 | Weiner et al. | |
| 4,696,288 A | 9/1987 | Kuzmak et al. | |
| 4,708,140 A | 11/1987 | Baron | |
| 4,716,154 A | 12/1987 | Malson et al. | |
| 4,753,086 A | 6/1988 | Schmidt | |
| 4,760,837 A | 8/1988 | Petit | |
| 4,803,075 A | 2/1989 | Wallace et al. | |
| 4,881,939 A | 11/1989 | Newman | |
| 4,883,467 A | 11/1989 | Franetzki et al. | |
| 4,886,787 A | 12/1989 | de Belder et al. | |
| 4,896,787 A | 1/1990 | Delamour et al. | |
| 4,915,690 A | 4/1990 | Cone et al. | |
| 4,925,446 A | 5/1990 | Garay et al. | |
| 4,944,487 A | 7/1990 | Holtermann | |
| 4,944,659 A | 7/1990 | Labbe et al. | |
| 4,958,791 A | 9/1990 | Nakamura | |
| 4,969,899 A | 11/1990 | Cox, Jr. | |
| 4,994,019 A | 2/1991 | Fernandez et al. | |
| 5,045,060 A | 9/1991 | Melsky et al. | |
| 5,074,868 A | 12/1991 | Kuzmak | |
| 5,084,061 A | 1/1992 | Gau et al. | |
| 5,091,171 A | 2/1992 | Yu et al. | |
| 5,116,652 A | 5/1992 | Alzner | |
| 5,120,313 A | 6/1992 | Elftman | |
| 5,143,724 A | 9/1992 | Leshchiner et al. | |
| 5,152,770 A | 10/1992 | Bengmark et al. | |
| 5,160,338 A | 11/1992 | Vincent | |
| 5,188,609 A | 2/1993 | Bayless et al. | |
| 5,224,494 A | 7/1993 | Enhorning | |
| 5,226,429 A | 7/1993 | Kuzmak | |
| 5,246,456 A | 9/1993 | Wilkinson | |
| 5,246,698 A | 9/1993 | Leshchiner et al. | |
| 5,259,399 A | 11/1993 | Brown | |
| 5,326,349 A | 7/1994 | Baraff | |
| 5,343,894 A | 9/1994 | Frisch et al. | |
| 5,356,883 A | 10/1994 | Kuo et al. | |
| 5,360,445 A | 11/1994 | Goldowsky | |
| 5,391,156 A | 2/1995 | Hildwein et al. | |
| 5,399,351 A | 3/1995 | Leshchiner et al. | |
| 5,449,363 A | 9/1995 | Brust et al. | |
| 5,449,368 A | 9/1995 | Kuzmak | |
| 5,458,568 A | 10/1995 | Racchini et al. | |
| 5,509,888 A | 4/1996 | Miller | |
| 5,531,716 A | 7/1996 | Luzio et al. | |
| 5,535,752 A | 7/1996 | Halperin et al. | |
| 5,554,113 A | 9/1996 | Novak et al. | |
| 5,562,714 A | 10/1996 | Grevious | |
| 5,601,604 A | 2/1997 | Vincent | |
| 5,607,418 A | 3/1997 | Arzbaecher | |
| 5,633,001 A | 5/1997 | Agerup | |
| 5,653,718 A | 8/1997 | Yoon | |
| 5,658,298 A | 8/1997 | Vincent et al. | |
| 5,676,162 A | 10/1997 | Larson, Jr. et al. | |
| 5,695,504 A | 12/1997 | Gifford, III et al. | |
| 5,704,893 A | 1/1998 | Timm | |
| 5,713,911 A | 2/1998 | Racenet et al. | |
| 5,733,257 A | 3/1998 | Sternby | |
| 5,748,200 A | 5/1998 | Funahashi | |
| 5,766,232 A | 6/1998 | Grevious et al. | |
| 5,769,877 A | 6/1998 | Barreras, Sr. | |
| 5,785,295 A | 7/1998 | Tsai | |
| 5,817,113 A | 10/1998 | Gifford, III et al. | |
| 5,827,529 A | 10/1998 | Ono et al. | |
| 5,833,698 A | 11/1998 | Hinchliffe et al. | |
| 5,861,014 A | 1/1999 | Familoni | |
| RE36,176 E | 3/1999 | Kuzmak | |
| 5,886,042 A | 3/1999 | Yu et al. | |
| 5,904,697 A | 5/1999 | Gifford, III et al. | |
| 5,910,149 A | 6/1999 | Kuzmak | |
| 5,928,195 A | 7/1999 | Malamud et al. | |
| 5,938,669 A | 8/1999 | Klaiber et al. | |
| 5,944,696 A | 8/1999 | Bayless et al. | |
| 5,944,751 A | 8/1999 | Laub | |
| 5,993,473 A | 11/1999 | Chan et al. | |
| 6,013,679 A | 1/2000 | Kuo et al. | |
| 6,024,340 A | 2/2000 | Lazarus et al. | |
| 6,024,704 A | 2/2000 | Meador et al. | |
| 6,048,309 A | 4/2000 | Flom et al. | |
| 6,067,991 A | 5/2000 | Forsell | |
| 6,074,341 A | 6/2000 | Anderson et al. | |
| 6,074,378 A | 6/2000 | Mouri et al. | |
| 6,083,249 A | 7/2000 | Familoni | |
| 6,090,131 A | 7/2000 | Daley | |
| 6,102,678 A | 8/2000 | Peclat | |
| 6,102,922 A | 8/2000 | Jakobsson et al. | |
| 6,171,321 B1 | 1/2001 | Gifford, III et al. | |
| 6,193,734 B1 | 2/2001 | Bolduc et al. | |
| 6,203,523 B1 | 3/2001 | Haller et al. | |
| 6,210,345 B1 | 4/2001 | Van Brunt | |
| 6,210,347 B1 | 4/2001 | Forsell | |
| 6,221,024 B1 | 4/2001 | Miesel | |
| 6,224,857 B1 | 5/2001 | Romeo et al. | |
| 6,306,088 B1 | 10/2001 | Krausman et al. | |
| 6,327,503 B1 | 12/2001 | Familoni | |
| 6,371,965 B2 | 4/2002 | Gifford, III et al. | |
| 6,372,494 B1 | 4/2002 | Naughton et al. | |
| 6,383,218 B1 | 5/2002 | Sourdille et al. | |
| 6,383,219 B1 | 5/2002 | Telandro et al. | |
| 6,387,105 B1 | 5/2002 | Gifford, III et al. | |
| 6,417,750 B1 | 7/2002 | Sohn | |
| 6,418,934 B1 | 7/2002 | Chin | |
| 6,419,696 B1 | 7/2002 | Ortiz et al. | |
| 6,432,040 B1 | 8/2002 | Meah | |
| 6,439,539 B1 | 8/2002 | Powell | |
| 6,443,957 B1 | 9/2002 | Addis | |
| 6,443,965 B1 | 9/2002 | Gifford, III et al. | |
| 6,450,173 B1 | 9/2002 | Forsell | |
| 6,450,946 B1 | 9/2002 | Forsell | |
| 6,451,034 B1 | 9/2002 | Gifford, III et al. | |
| 6,453,907 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |
| 6,454,785 B2 | 9/2002 | De Hoyos Garza | |
| 6,457,801 B1 | 10/2002 | Fish et al. | |
| 6,460,543 B1 | 10/2002 | Forsell | |
| 6,461,293 B1 | 10/2002 | Forsell | |
| 6,463,935 B1 | 10/2002 | Forsell | |
| 6,464,628 B1 | 10/2002 | Forsell | |
| 6,470,892 B1 | 10/2002 | Forsell | |
| 6,474,584 B2 | 11/2002 | Ekich | |
| 6,475,136 B1 | 11/2002 | Forsell | |
| 6,485,496 B1 | 11/2002 | Suyker et al. | |
| 6,491,704 B2 | 12/2002 | Gifford, III et al. | |
| 6,491,705 B2 | 12/2002 | Gifford, III et al. | |
| 6,511,490 B2 | 1/2003 | Robert | |
| 6,517,556 B1 | 2/2003 | Monassevitch | |
| 6,527,701 B1 | 3/2003 | Sayet et al. | |
| 6,547,801 B1 | 4/2003 | Dargent et al. | |
| 6,565,582 B2 | 5/2003 | Gifford, III et al. | |
| 6,579,301 B1 | 6/2003 | Bales et al. | |
| 6,601,604 B1 | 8/2003 | Cooper | |
| 6,615,084 B1 | 9/2003 | Cigaina | |

| Patent No. | Date | Name |
|---|---|---|
| 6,627,620 B1 | 9/2003 | Nielsen |
| 6,630,486 B1 | 10/2003 | Royer |
| 6,632,239 B2 | 10/2003 | Snyder et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredericks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,767,924 B2 | 7/2004 | Yu et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pierce |
| 6,940,467 B2 | 9/2005 | Fischer et al. |
| 6,966,875 B1 | 11/2005 | Longobardi |
| 7,017,583 B2 | 3/2006 | Forsell |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,054,690 B2 | 5/2006 | Imran |
| 7,058,434 B2 | 6/2006 | Wang et al. |
| 7,060,080 B2 | 6/2006 | Bachmann |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,204,821 B1 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrum |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave et al. |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |

| | | |
|---|---|---|
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neil |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161139 A1 | 7/2006 | Levine et al. |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0293716 A1 | 12/2007 | Baker et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |

| Pub. No. | Date | Name |
|---|---|---|
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2010/0010291 A1 | 1/2010 | Birk et al. |
| 2010/0049224 A1 | 2/2010 | Vargas |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312046 A1 | 12/2010 | Lau et al. |
| 2010/0312147 A1 | 12/2010 | Gertner |
| 2010/0324358 A1 | 12/2010 | Birk et al. |
| 2011/0201874 A1 | 8/2011 | Birk et al. |

FOREIGN PATENT DOCUMENTS

| | | |
|---|---|---|
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2074972 | 7/2009 |
| EP | 2095796 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/85071 | 11/2001 |
| WO | WO 02/05753 | 1/2002 |
| WO | WO 02/09792 | 2/2002 |
| WO | WO 02/019953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 7/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.
Dixon et al.; "Pregnancy After Lap-Band Surgery: Management of the Band to Achieve Healthy Weight Outcomes"; Obesity Surgery; V. 11, pp. 59-65; 2001.
Neary et al.; "Peptide YY(3-36) and Glucagon-Like Peptide-1$_{(7-36)}$ Inhibit Food Intake Additively"; Endocrinology; V.146; pp. 5120-5127; 2005.
Padidela et al.; "Elevated basal and post-feed glucagon-like petide 1 (GLP-1) concentrations in the neonatel period"; European Journal of Endocrinology; v. 160; pp. 53-58; 2009.
Shi et al.; "Sexually Dimorphic Responses to Fat Loss After Caloric Restriction or Surgical Lipectomy"; Am. J. Physiol. Endocrinol. Metab.; V. 293; E316-E326; 2007.
Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.
"Innovative medical devices and implants"; LGSP medical futures, p. 5.
Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.
Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Lap-Band Adjustable Gastric Banding System, Inamed Health, pub., pp. 1-115; Aug. 28, 2003.
Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.
Corno et al.; "A new implantable device for telemetric control of pulmonary blood flow"; New ideas; received Apr. 24, 2004; received in revised form Jul. 12, 2002; 10 pages.
Corno et al.; "FlowWatchTM in clipped and inclipped position"; Interact Cardio Vase Thorac Surg 2002; 1:46-49; Copyright @ 2002 The European Asociation for Cardio-thoracic Surgery; 1 page.
Cummings et al.; "Plasma Ghrelin Levels After Diet-Induced Weight Loss or Gastric Bypass Sugery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.
Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.
Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J Gastrointest Surg.; V.13; pp. 775-783, 2009.

Kesty et al.; "Hormone-based therapies in the regulation of fuel metabolism and body weight"; Expert Opin. Biol. Ther.; V. 8; No. 11; pp. 1733-1747; 2008.

Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.

Kojima et al.; "A role for pancreatic polypeptide in feeding and body weight regulation." Peptides; V. 28; pp. 459-463; 2007.

Kulicke et al. "Visco-Elastic Propeerties of Sodium Hyaluronate Solutions," American Institute of Physics; pp. 585-587; 2008.

Lap-Band AP System Adjustable Gastric Banding System With OmniformTM Design: Directions for Use (DFU); Allergan, 16 pages; 2009.

Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.

Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.

Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.

Mathus-Vliegen et al. "Treating Morbid and Supermorbid Obesity" International Journal of Gastroenterology; V. 5, No. 1, pp. 9-12; 2000.

Medeiros et al.; "Processing and metabolism of Peptide-YY: Pivotal roles of Dipeptidase-IV, Aminopeptidase-P, and Endopeptidase-24. 11"; Endocrinology; V. 134, No. 5; pp. 2088-2094; 1994.

Naslund et al. "Pranidal subcutaneous injections of glucagon-like peptide-1 cause weight loss in obese human subjects"; British Journal of Nutrition; V. 91; pp. 439-446; 2004.

Potier et al.; "Protein, amino acids, and the control of food intake"; Current Opinion in Clinical Nutrition and Metabolic Care; V. 12; pp. 54-58; 2009.

Qjan et al.; "Pulmonary delivery of a GLP-1 receptor agonist, BMS-686117"; International Journal of Pharmaceutics; V. 366; pp. 218-220; 2008.

Rang et al.; "Pharmacology"; V. 5; pp. 203, 397, 402, 524; 2004.

Raybould et al.; "Integration of Postprandial Gastrointestinal Tract: Role of CCK and Sensory Pathways"; Annals of New York Academy of Science; pp. 143-156; 1994.

Renshaw et al. "Peptide YY: A Potential Therapy for Obesity"; Current Drug Targets; V. 6; pp. 171-179; 2005.

Sannino et al.; "Crosslinking of Cellulose Derivatives and Hyaluronic Acid with Water-Soluble Carbodiimide" Polymer 46; pp. 11206-11212; 2005.

Shechter et al.; "Reversible PEGylation of peptide YY3-36 prolongs its inhibition of food intake in mice"; FEBS Letters; V. 579; pp. 2439-2444; 2005.

Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.

Small et al.; "Gut hormones and the control of appetite"; TRENDS in Endocrinology and Metabolism; V. 15. No. 6; pp. 259-263; Aug. 2004.

Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.

Tezel; "The Science of Hyaluronic Acid Dermal Fillers," Journal of Cosmetic and Laser Therapy (2008) 10: pp. 35-42.

Tolhurst et al.; "Nutritional regulation of glucagon-like peptide1 secretion"; J. Physiol.; V. 587, No. 1; pp. 27-32; 2009.

Totte et al.; "Weight Reduction by Means of Intragastric Device: Experience with the Bioenterics Intragastric Balloon"; Obesity Surgery; V. 11, pp. 519-523; 2001.

Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.

Tseng et al; "Peptide YY and cancer: Current findings and potential clinical applications"; Peptides; V. 23; pp. 389-395; 2002.

Valassi et al.; "Neuroendocrine control of food intake"; Nut. Metab. & Cariovasc. Disease; V. 18; pp. 158-168; 2008.

Van Der Lely et al.; "Biological, Physiological, Pathophysiological Aspects of Ghrelin"; Endocrine Reviews; V. 25, No. 3; pp. 426-457; 2004.

Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.

Wahlen et al.; "The BioEnterics Intragastric Balloon (BIB): How to Use It"; Obesity Surgery; V. 11; pp. 524-527; 2001.

Wang et al.; "Plasma Ghrelin Modulation in Gastric Band Operation and Sleeve Gastrectomy"; Obes. Surg.; pp. 357-362; 2008.

Weiner et al.; "Preparation of Extremely Obese Patients for Laparoscopic Gastric Banding by Gastric Balloon Therapy"; Obesity Surgery; V. 9, pp. 261-264, 1999.

Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.

Yuzuriha et al.; "Gastrointestinal Hormones (anorexigenic peptide YY and orexigenic ghrelin) influence neural tube development"; FASEB J.; V. 21; pp. 2108-2112; 2007.

* cited by examiner

FATIGUE-RESISTANT GASTRIC BANDING DEVICE

CROSS REFERENCE TO RELATED APPLICATIONS

This application is a continuation of and claims the benefit and priority of U.S. application Ser. No. 10/492,784, filed Apr. 18, 2005, now U.S. Pat. No. 7,811,298, which claims the benefit and priority of PCT Application No. PCT/US2003/026678, filed Aug. 26, 2003, which claims the benefit and priority of U.S. Provisional Patent Application No. 60/407,219, filed Aug. 28, 2002, the entire disclosure of each of these applications is incorporated herein by reference.

BACKGROUND

1. Field of the Invention

The present invention relates generally to surgically implanted gastric bands for encircling the stomach having notches, ribs and/or chambers in the inflatable portion to reduce fatigue or crease fold failure in the device, while increasing the range of adjustment. A method for treating morbid obesity utilizing a fatigue-resistant gastric banding device is also disclosed.

2. Description of the Related Art

A belt-like gastric band for encircling the stomach to control morbid obesity is disclosed by Vincent in U.S. Pat. No. 5,601,604, incorporated herein by reference. The band comprises a belt that can be passed around the stomach and locked into an encircling position in order to create a stoma opening within the stomach. An adjustable portion of the band comprises an inflatable member, which permits fine adjustment of the stoma opening after the stoma is created by locking the band in place. The stoma opening may be adjusted by injecting or withdrawing a fluid into or from an inflatable member. The means for injecting the fluid into the inflatable member usually comprises a fill port located beneath the skin that can be accessed extracorporeally by transdermal injection. Thus, following implantation, the gastric band can be adjusted to enlarge or reduce the stoma as required.

The gastric band is implanted surgically, via open or laparoscopic surgery, which may involve placement of a calibrating apparatus in the stomach to position the stoma and size the pouch created above the stoma. The gastric band is imbricated in position about the stomach to prevent slippage, usually by gastro-gastric sutures (i.e. tissue is wrapped over the band and sutured to itself).

As disclosed by Vincent, the inflatable member or shell is preferably substantially coextensive with an inner stomach-facing surface of the gastric band. Furthermore, it has been observed that the inflatable member should not wrinkle or fold when adjusted, so as to present a substantially smooth contour along the inner circumference. This ensures not only that stomach tissue will not be pinched by the inflatable member, which could lead to discomfort or necrosis, but also protects the shell from a phenomenon known as crease fold failure, which may occur if it is inflated beyond its intended range of adjustment. In the field, it has been observed that silicone or other elastomeric materials commonly used in the manufacture of gastric bands can fatigue or fail if repeatedly compressed, folded, wrinkled, buckled under stress or creased by, for example, over-inflation. This failure mode, which may include abrasion of the opposing surfaces against one another, abrasion of the inner surface of the fold "peak" against the opposing chamber wall, or fatigue of the material at folder intersections (the most highly-stressed areas), is sometimes referred to as crease fold failure.

In some cases, it has also been noted that existing adjustable gastric bands do not provide the overall size or range of adjustment desirable for use in particular patients. For instance, existing gastric bands may be either too large or too small to encircle a patient's stomach, while still allowing for a properly sized stoma. This may be due, for instance, to variations from patient to patient and their individual internal physiologies. Thus, gastric bands are now available in several different sizes, measured according to the circumference of the band (e.g. 9.75 cm, 11 cm, etc.). But due to variations in not only patient physiology, but also in the location and encircling position of the band, the surgical technique used, etc., it may not be evident what size band is necessary until a patient is undergoing surgery. Rather than have a variety of different sizes of gastric bands on hand during the surgical procedure, it would be desirable to have one universal size gastric band available that is adjustable over a wider range than those bands known in the prior art.

If the overall size of the gastric band is increased, the inflatable shell portion may not be capable of being adjusted to form a relatively small stoma without creases, wrinkles or folds forming on the inner stomach-facing surface, which may lead to fatigue or failure of the inflatable member, necessitating additional surgery. It would therefore be desirable to provide a universal size of a fatigue-resistant gastric band having an inflatable member that can be adjusted over a wide range of stoma openings.

OBJECTS OF THE INVENTION

The foregoing demonstrates a need for a surgically implantable gastric band having a universal size and offering a range of adjustability suitable for use in a variety of patients.

It is therefore an object of the present invention to provide a gastric band universally sized for use in patients with varying internal physiologies.

It is another object of the present invention to provide a gastric band having an inflatable member adjustable over a wider range of stoma openings than currently available devices.

It is yet another object of the present invention to provide a gastric band having an inflatable member that is substantially coextensive with an inner stomach-facing surface of the gastric band.

Still another object of the present invention is to provide a gastric band having an inflatable member that does not wrinkle or fold when adjusted over a wide range, so as to present a substantially smooth contour along the inner circumference, and to avoid fatigue or failure of the member itself.

Various other objects, advantages and features of the present invention will become readily apparent from the ensuing detailed description and the novel features will be particularly pointed out in the appended claims.

SUMMARY OF THE INVENTION

A preferred embodiment of the invention provides a fatigue-resistant gastric banding device for the treatment of morbid obesity. The device has a gastric band suited for laparoscopic placement around the stomach of a patient to form an adjustable stoma opening. The gastric band has a multi-chambered inflatable member for adjusting the inner circumference of the band. The inflatable member is preferably substantially coextensive with an inner stomach-facing surface of the gastric band. The inflatable member is chambered so as to not wrinkle or fold when adjusted over its range of adjustment, thereby presenting a substantially smooth contour along the inner circumference and reducing fatigue or failure of the device.

Another embodiment of the present invention is a gastric band having an inflatable shell including a plurality of chambers. Separating the chambers is at least one notch and/or reinforcing rib. Upon inflation of the gastric band, the chambers, ribs and/or notches eliminate creasing, folding or wrinkling of said inflatable shell, thereby reducing fatigue on the device.

Yet another embodiment of the present invention is a method of treating morbid obesity. The method of treatment includes the steps of providing a gastric band having an inflatable shell with a plurality of chambers, ribs and/or notches. A further step requires placing the gastric band around the stomach of a patient to be treated for morbid obesity, and inflating the gastric band to form a stoma.

The fatigue-resistant gastric band of the present invention may be adjusted by adding fluid to or removing fluid from the chambered inflatable member or shell by means of a subcutaneous access port, via a remotely controllable pump, using pressurized fluid or through other means well known to one skilled in the art.

BRIEF DESCRIPTION OF THE DRAWINGS

The following detailed description given by way of example, but not intended to limit the invention solely to the specific embodiments described, may best be understood in conjunction with the accompanying drawings in which.

DETAILED DESCRIPTION

Figure 1:
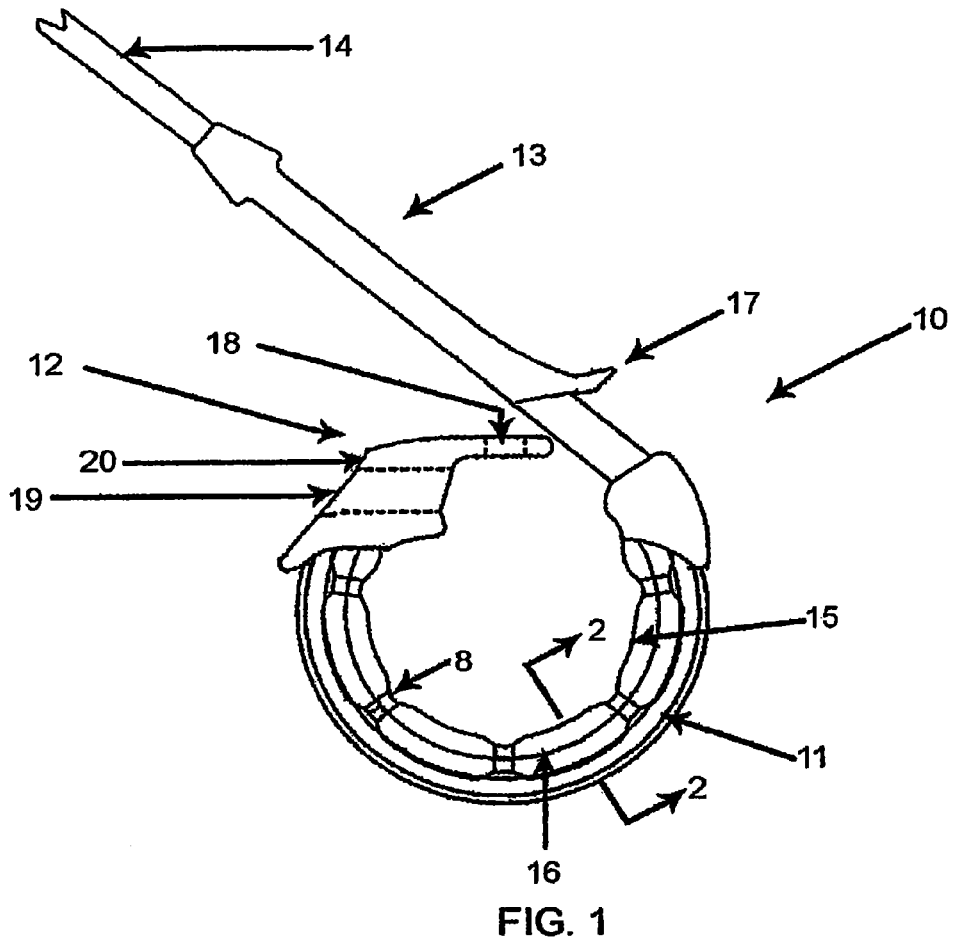
FIG. 1 is a top view of a gastric band according to one embodiment of the present invention.

An inflatable gastric band 10 according to the present invention is shown in FIG. 1. The gastric band 10 has a body portion 11 and an inflatable portion or shell 16. The body portion 11 has a head end 12 and a tail end 13. The head end 12 of the body portion 11 has a buckle 19 with a pull-tab 18. The tail end 13 includes a belt tab 17. Upon insertion of the tail end 13 including a fill tube 14 through the buckle 19, the tail end 13 is drawn through the buckle 19 until the belt tab 17 catches on the exit side 20. In this position the gastric band 10 is releasably locked in a closed loop position and secured by the buckle 19 and the belt tab 17.

The fill tube 14, which is generally a tube having a single lumen (not shown) coextensive therewith, is connected to an end of the gastric band 10. In FIG. 1 it is shown attached to the tail end 13 and in fluid communication with an inflatable shell 16. It will be apparent to one of skill in the art that other arrangements of the fill tube 14 could be made including attachment to the head end 12 without departing from the scope of the present invention.

Figure 2:
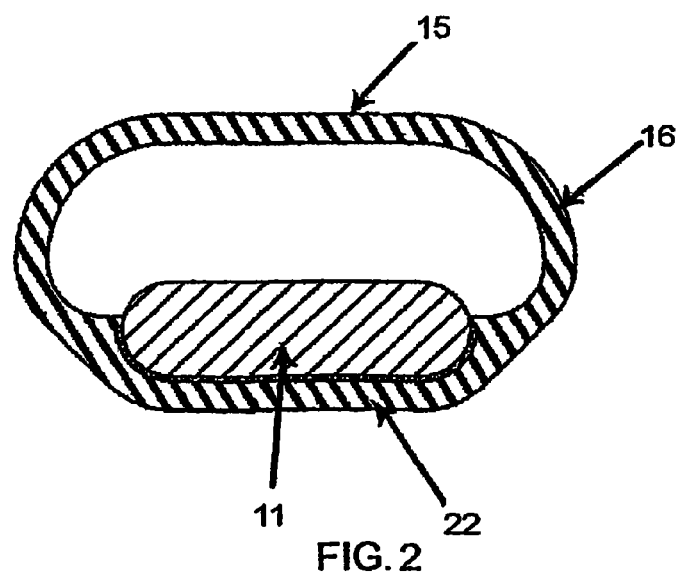
FIG. 2 is a cross-sectional view of the gastric band shown in FIG. 1 taken along line 2-2.

The inflatable shell 16 is formed to receive the body portion 11 as shown in FIG. 2, which is a cross sectional view of FIG. 1 taken along line 2-2. The inflatable shell 16 is preferably substantially coextensive with the body portion 11, as shown in FIG. 1. The body portion 11 may be attached to the interior of the inflatable shell 16 through the use of adhesives compatible for use within the body or other methods known to those skilled in the art of implantable medical device manufacture. The inflatable shell 16 includes an inner stomach-facing surface 15 that forms a stoma when placed around the stomach. It is this surface that has traditionally been the location of failure due to crease fold fatigue.

Figure 3:
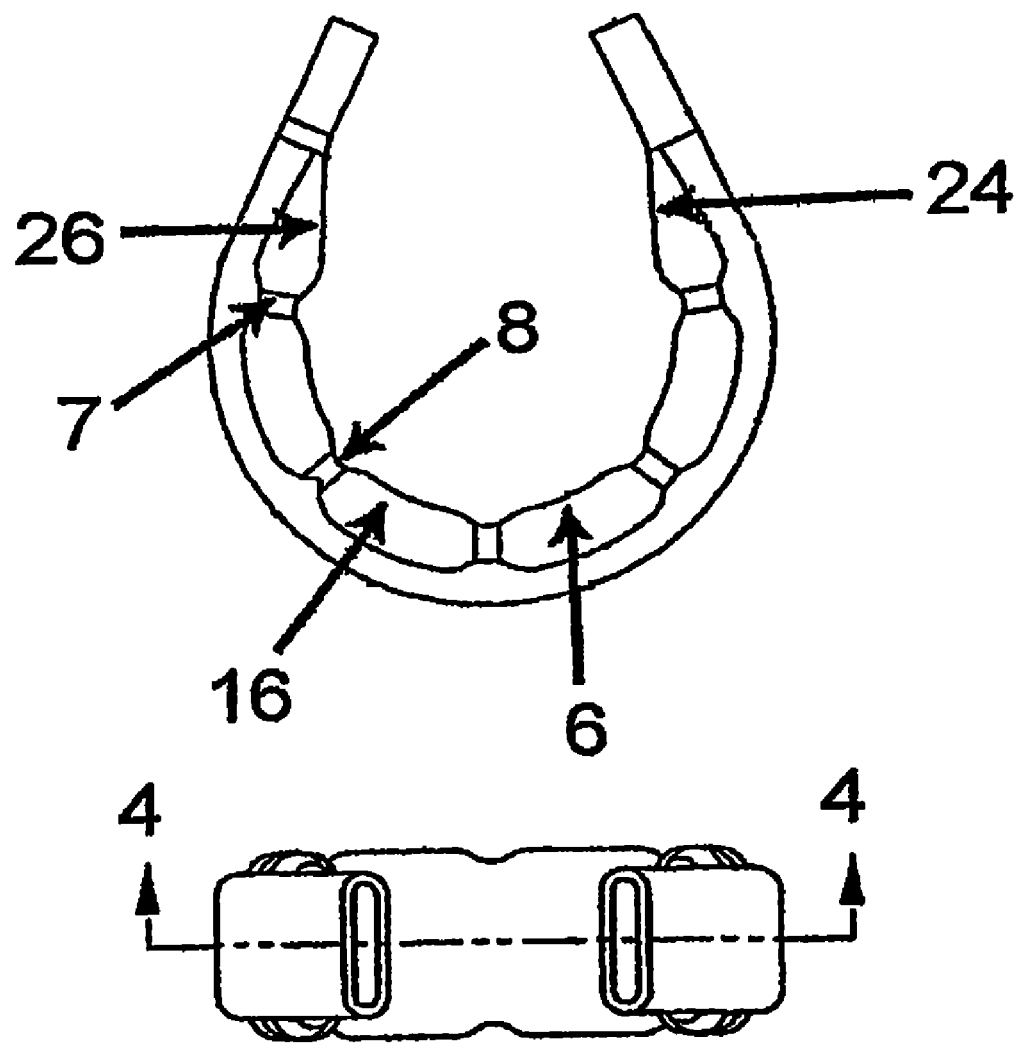
FIG. 3 is a top and side view of the encircling portion of a fatigue-resistant inflatable shell of the gastric band of FIG. 1.

To reduce the potential for crease fold failure or high stresses in the inner surface 15, the inflatable shell 16 has pre-formed stress-reducing notches 8 separating chambers 6. FIG. 3 shows a top view of the inflatable shell 16 of gastric band 10 with plurality of chambers 6 each separated by a respective notch 8. FIG. 3 differs from FIG. 1 in that it shows just the inflatable shell 16 without the inner portion 11 of the gastric band 10.

Figure 4:
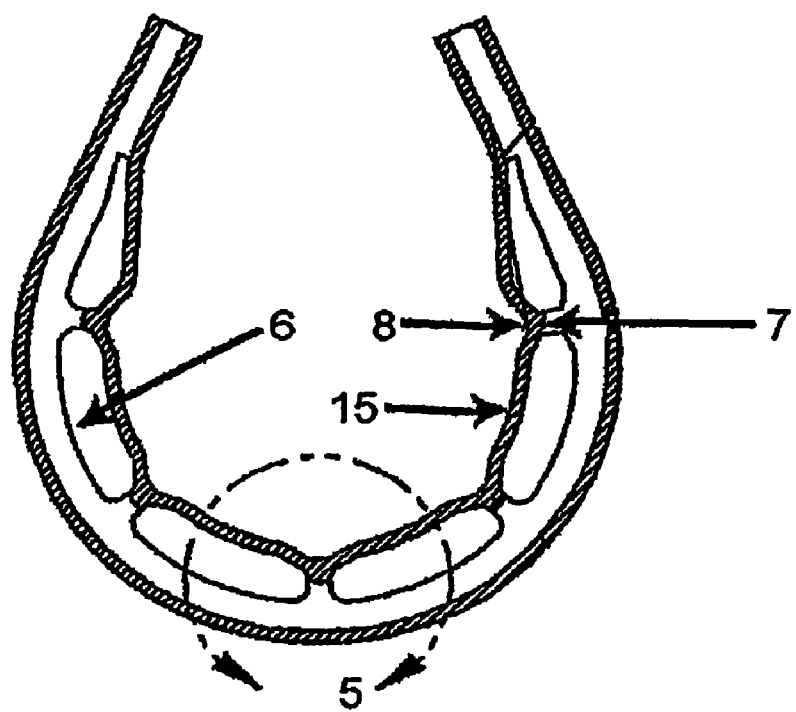
FIG. 4 is a cross-sectional top view of the fatigue-resistant inflatable shell of FIG. 3 taken along line 4-4.

Similarly, FIG. 4 shows a cross-sectional top view of the inflatable shell 16 shown in FIG. 3. In FIG. 4, the inside of the inflatable shell 16 is depicted with reinforcing ribs 7 at each of the notches 8 separating each of the chambers 6. However, as shown in FIG. 3, the first chamber 24 and the last chamber 26 of the inflatable shell 16 may be formed with only one rib 7.

The band may be formed with a single notch 8 along the inner stomach-facing surface 15 of the inflatable shell 16, or more preferably, with multiple notches 8. Similarly, the band may be formed with a single reinforcing rib 7 inside the inflatable shell 16, or more preferably, with multiple ribs 7. Most preferably, the inflatable shell 16 is formed with corresponding ribs 7 and notches 8. The notches 8, chambers 6, and ribs 7 are formed in the inflatable shell 16 during the manufacturing process and are a feature of the inflatable shell 16 of the gastric band 10 whether filled or unfilled (i.e. whether the band is inflated or un-inflated). This helps to ensure that upon initial positioning of the gastric band 10 there is no pinching of the stomach.

Figure 6:
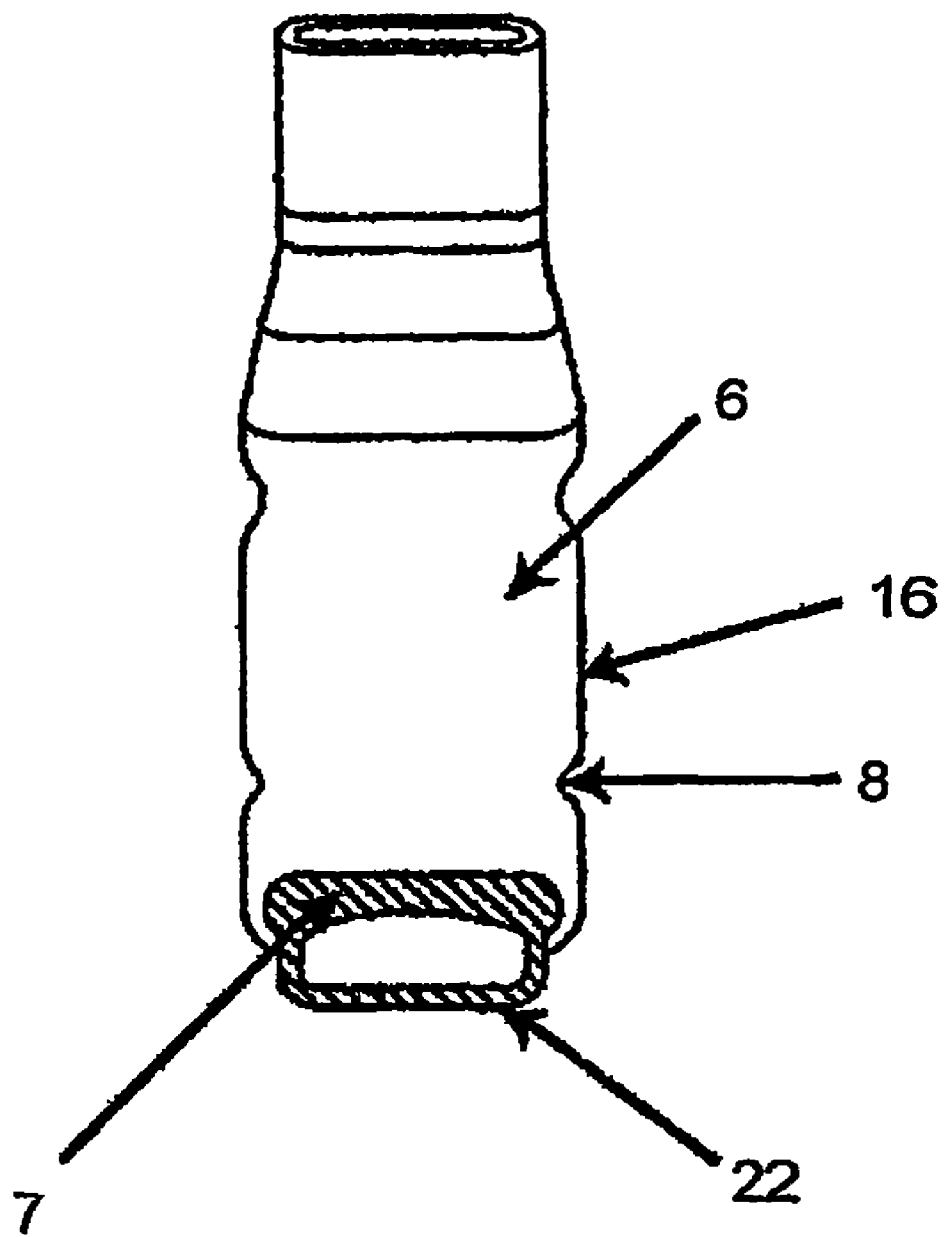
FIG. 6 is a cross-sectional view of the fatigue-resistant inflatable shell of FIG. 3 taken along line 6-6 showing the relative thickness of a reinforcing rib.
Figure 7:
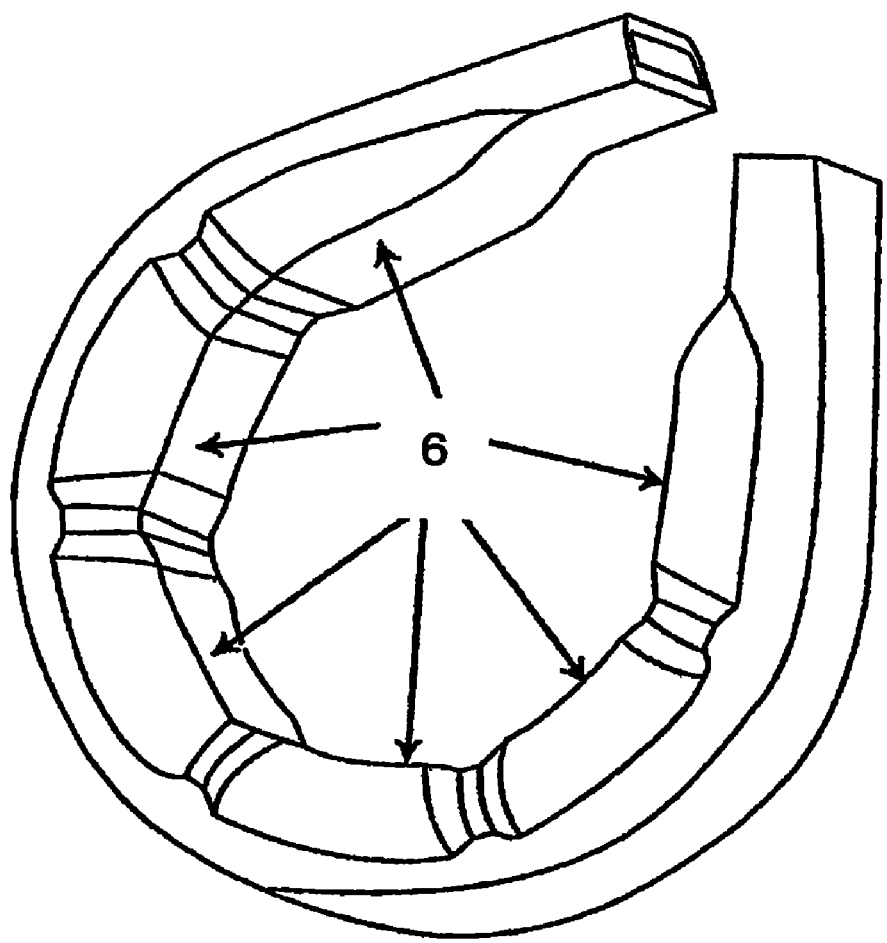
FIG. 7 is a perspective view of the encircling portion of a fatigue-resistant inflatable shell of a gastric band according to the present invention.
Figure 8:
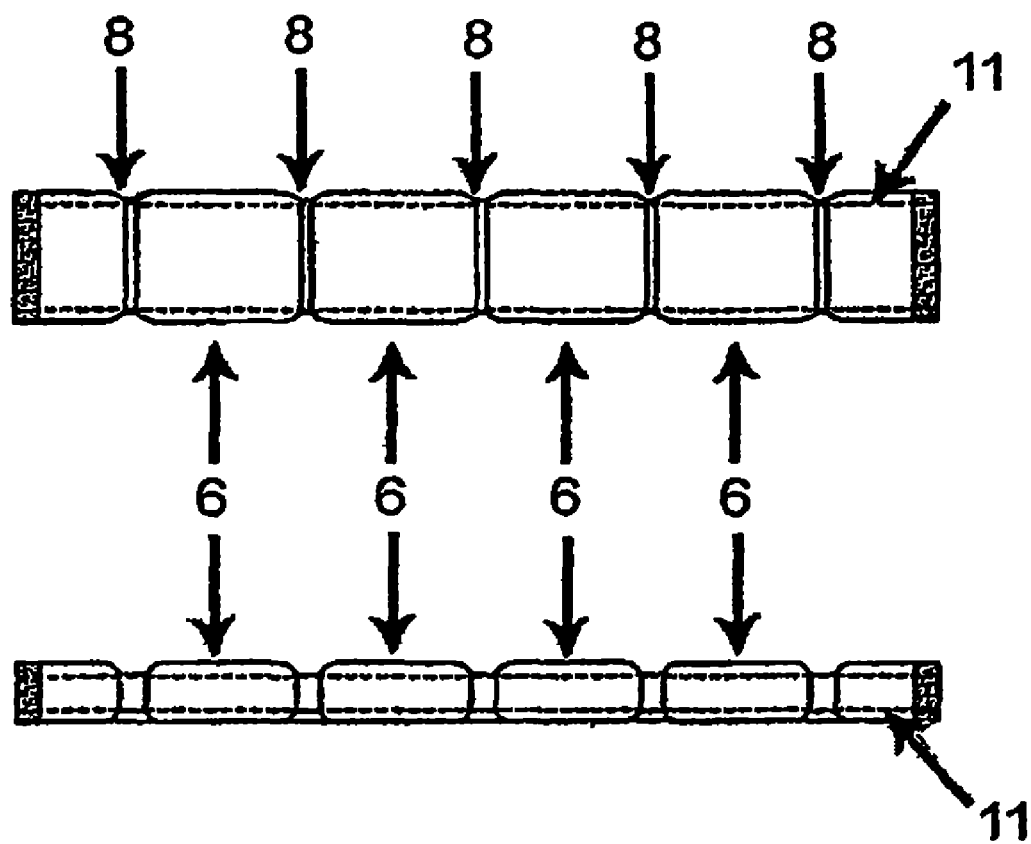
FIG. 8 is a top and side view of a portion of the gastric band of FIG. 1 straightened to show the width and projection of the chambers in relation to the inner band portion.

FIG. 6 shows a cross sectional view of the inflatable shell 16 of FIG. 3 taken along line 6-6. In FIG. 6, the thickness of the rib 7 can be seen relative to the thickness of the inflatable shell 16. FIG. 6 also shows that the width of the chambers 6 may extend beyond the width of an outer surface 22 of the inflatable shell 16. Similarly, FIG. 8 shows the chambers 6 extending beyond the width of the body portion 11 (designated by the dotted line). The greater size of the chambers 6 relative to the body portion 11 helps to evenly distribute the forces applied to the stomach through the inflation of the gastric band 10.

Figure 5:
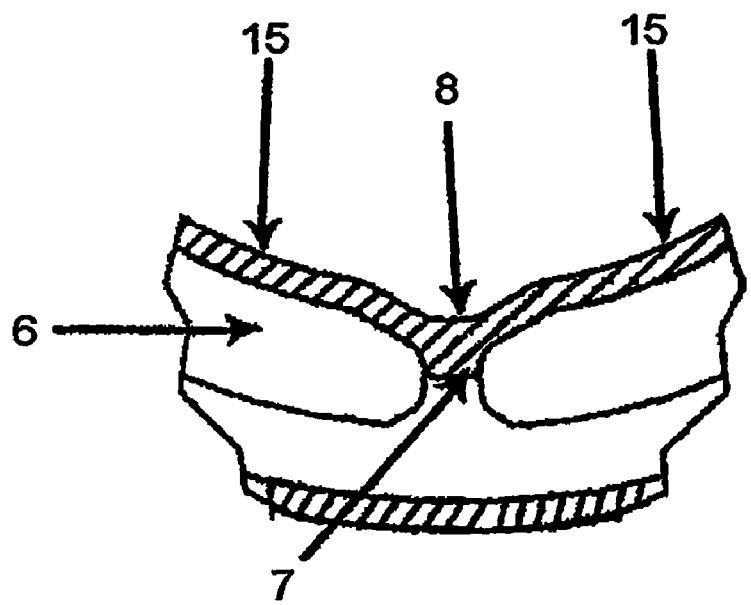
FIG. 5 is a close up cross-sectional view of a convolution point of the fatigue-resistant inflatable shell of FIG. 4 taken in area 5.

FIG. 5 shows a close-up view of a notch 8 and rib 7 of the inflatable shell 16. Also shown in FIG. 5 are chambers 6 on either side of the rib 7. From FIG. 5, it can be seen that the portions of the inner surface 15 immediately adjacent to the notches 8 will not come in contact with one another upon inflation of a gastric band 10 having an inflatable shell 16 so designed. This prevents wear and rubbing of the inner surface 15. Also as a result of the notch 8, a crease will not form in the inner surface 15 of the inflatable shell 16. Further, because of this, the chamber 6 can be inflated to a much greater volume forming a smaller stoma than similar sized gastric bands known in the prior art.

The effects of the notch 8 can be described as follows: the notch 8 acts as a pre-formed crease in the inflatable shell 16. The notch 8 acts similarly to the crease that may form in gastric bands known in the prior art as it provides a point around which the body portion 11 is allowed to bend the inner surface 15 of the gastric band 10 to form a substantially circular band. One with basic geometry skills will understand that the inner surface 15 and the body portion 11 have substantially similar lengths. As a result of this, if the body portion 11 and the inflatable shell 16 are not pre-formed in a circle, when they are subsequently bent into a circular form, the interior surface 15 must in some fashion eliminate a portion of its overall length to form a circle having a smaller inner circumference than outer circumference. This reduction in circumference has heretofore occurred in prior art gastric bands through the formation of undesirable creases on the inner stomach-facing surface of the gastric band, resulting in a reduced range of inflation for such bands. The formation of these creases alleviates the material stresses in forming the circular shape, but causes point loading at the top and bottom of the creases as well as providing a point of friction between two facing sides of the crease. By forming the inflatable shell 16 in a circle with pre-formed notches 8, the aforementioned stresses are drastically reduced because the notch 8, alone or in combination with a rib 7, is formed in a fashion that prevents opposing sides of the notch 8 from buckling and reduces stress, while allowing for a great range of inflation versus prior art devices. Additionally, the effects of the point loading associated with the extremities of the crease can be alleviated by the notch 8, especially when the notch 8 is formed in conjunction with a reinforcing rib 7.

In practice, the gastric band is placed in an encircling position around the stomach using known surgical techniques, including, preferably laparoscopy. Laparoscopic placement is accomplished by introducing the fill tube 14 through a laparoscopic cannula (not shown) into the patient's abdomen. Laparoscopic placement begins with blunt dissection behind the stomach, usually two to three centimeters below the gastro-esophageal junction. Typically, the end of the fill tube 14 and the tail end 13 are passed around the stomach and drawn through the buckle 19, past the exit side 20 so that the belt tab 17 and the buckle 19 are releasably locked together. In this sense, the band is a "one-size-fits-all" device—like that described by Vincent—but because of its notched design, the gastric band is adjustable over a greater range without creasing or folding than Vincent and other known prior art bands.

The stoma—the narrow opening in the stomach created by the band—may be adjusted after the band is secured in this single position. Prior art gastric bands employ an adjustable balloon portion that is used for post-operative adjustment of the stoma as necessary. These adjustable balloons, as discussed above, are prone to creasing. The pre-formed notches 8, chambers 6 and ribs 7 of the inflatable gastric band 10 described herein provide for increased fill volumes, e.g. up to 10 cc, without wrinkles or folds forming in the shell. As in the Vincent band, the inflatable shell 16 is preferably coextensive with the inner stomach-facing surface 15 of the band between the belt tab 17 and the buckle 19. The interior of the inflatable shell 16 is in fluid communication with an injection reservoir, remote pump, pressure reservoir or other adjustment means (not shown) via fill tube 14, as with prior art adjustable gastric bands. The inflatable shell 16 is gradually inflated with saline or other biocompatible fluid via the adjustment means such that the inflatable shell 16, and in particular the inner surface 15 thereof presses on and constricts the stomach underlying the band. This results in a decrease of the opening (stoma) inside the stomach directly under the encircling gastric band 10.

During inflation of the gastric band 10, the notches 8 and the ribs 7 resist deflection. At the same time, the chambers 6 do not comparatively resist deflection. This results in the areas of the inflatable shell 16 where the ribs 7 are located forming deeper notches 8 upon inflation. Accordingly, these notches 8 reduce the stresses in the inflatable shell 16 and reduce the potential for crease fold failure by eliminating contact between the two sides of the notch 8.

Despite the addition of the notches 8 and ribs 7, the gastric band 10 forms a substantially circular constriction around the stomach upon inflation. The chambers 6 of the inflatable shell 16 direct the locations of inflation. Because of the greater deflections of the inflatable shell 16 in the chambers 6 as compared to the area of the notches 8 and ribs 7, the gastric band 10, and in particularly the inner surface 15 is prevented from pinching the surface of the stomach between two chambers 6 when in its inflated state, thereby reducing the potential for patient discomfort and necrosis.

The gastric band 10, as shown in FIG. 1, allows for greater adjustability and fill volume range than current gastric bands, while reducing the potential for fatigue failure, crease fold failure, or pinching of the stomach. Through the use of the chambers 6, notches 8, and the elimination of crease points, the inflatable shell 16 is provided a greater expandable range and is able to produce a smaller opening without fear of pinching the stomach. Similarly, because the crease points are eliminated, the likelihood of crease fold failure is also reduced. It is the possibility of pinching the stomach, and the potential for crease-fold failure that limit the operable range of currently known devices. The reduction of these possibilities increases the range of the stoma opening that may be formed with a single gastric band, while safely treating the obese patient.

Another embodiment of the present invention is an inflatable gastric band with an inflatable shell that is separated into multiple, isolated inflatable compartments or chambers. The inflation of the isolated chambers may or may not be circular, but will not crease, wrinkle or fold. Each isolated chamber may be inflated separately or simultaneously with other isolated chambers and will expand without creasing, wrinkling or folding. A compartmentalized gastric band allows for even greater adjustability and fill volume ranges than current gastric bands while reducing the potential for fatigue failure or crease fold failure.

For example, it may be desirable to reduce the size of the stoma in a particular direction. In such instances, a chamber on that side of the gastric band could be inflated without changing the size of the remaining chambers. Accordingly, greater flexibility is available in a device having isolated chambers that may be independently filled and adjusted. Such an arrangement requires independent filling pathways for each chamber.

The design of the present invention has been described for use in gastric banding devices, but may also be incorporated into any inflatable or expandable device that uses silicone or other elastomeric or polymeric materials where there may be a concern over crease fold failure.

Although the invention has been particularly shown and described with reference to certain preferred embodiments, it will be readily appreciated by those of ordinary skill in the art that various changes and modifications may be made therein, without departing from the spirit and scope of the invention.

It is intended that the claims be interpreted as including the foregoing as well as various other such changes and modifications.

The invention claimed is:

1. A gastric band for the treatment of obesity suitable for laparoscopic placement around the stomach of a patient to create a stoma comprising:
   a body member configured to encircle the stomach; and
   an encompassing member having an inner wall and an outer wall wherein at least part of the body member is located between the inner wall and the outer wall of the encompassing member;
   the inner wall being continuous along a length of the body member encircling the stomach and having an inflatable portion, the inflatable portion including at least one notch defining a plurality of chambers, wherein the plurality of chambers have a width that extends beyond the width of the outer wall, and wherein the notch is configured to substantially eliminate at least one of creasing, folding or wrinkling along the inner wall.

2. The gastric band of claim 1, wherein the chambers are in fluid communication with one another.

3. The gastric band of claim 1, wherein the chambers are further defined by at least one rib adjacent to the at least one notch.

4. The gastric band of claim 1, wherein the chambers are in fluid isolation from one another.

5. The gastric band of claim 1, wherein the encompassing member is preformed in a curved configuration.

6. The gastric band of claim 1, wherein the body member is affixed to the outer wall.

7. A gastric band for the treatment of obesity suitable for laparoscopic placement around the stomach of a patient to create a stoma comprising:
   an elongated body member having connectible ends configured to encircle the stomach; and
   an encompassing member having an inner wall and an outer wall wherein at least part of the body member is located between the inner wall and the outer wall of the encompassing member and is affixed to the outer wall;
   the inner wall being continuous along a length of the body member encircling the stomach and having an inflatable portion, the inflatable portion including a plurality of notches defining a plurality of chambers, wherein the plurality of notches are configured to substantially eliminate at least one of creasing, folding or wrinkling along the inner wall.

8. The gastric band of claim 7, wherein the chambers extend beyond the width of the body member.

9. The gastric band of claim 7, further comprising a fill tube for inflation of the inflatable portion.

10. The gastric band of claim 7, wherein one of the connectible ends of the elongated body member further comprises a clasp for receiving a portion of the elongated body member to secure the gastric band in a curved configuration.

11. The gastric band of claim 10, wherein the connectible ends of the elongated body member are configured to be releasably secured.

12. The gastric band of claim 7, further comprising at least one rib.

* * * * *